US009196067B1

(12) United States Patent
Freed et al.

(10) Patent No.: US 9,196,067 B1
(45) Date of Patent: Nov. 24, 2015

(54) APPLICATION SPECIFIC TRACKING OF PROJECTION SURFACES

(71) Applicant: Rawles LLC, Wilmington, DE (US)

(72) Inventors: Ian W. Freed, Seattle, WA (US); William Spencer Worley, III, Half Moon Bay, CA (US)

(73) Assignee: Amazon Technologies, Inc., Seattle, WA (US)

( * ) Notice: Subject to any disclaimer, the term of this patent is extended or adjusted under 35 U.S.C. 154(b) by 224 days.

(21) Appl. No.: 13/786,221

(22) Filed: Mar. 5, 2013

(51) Int. Cl.
*G06T 15/00* (2011.01)
*G06T 11/60* (2006.01)
*G06F 3/01* (2006.01)
*G05D 1/02* (2006.01)
*A61B 5/00* (2006.01)

(52) U.S. Cl.
CPC ............... *G06T 11/60* (2013.01); *G06F 3/011* (2013.01); *A61B 5/0077* (2013.01); *G05D 1/0255* (2013.01)

(58) Field of Classification Search
CPC .... G05D 1/0255; A61B 5/0077; G06F 3/011; G06T 11/60
USPC ............. 345/419; 700/249, 245, 250; 348/46, 348/745
See application file for complete search history.

(56) References Cited

U.S. PATENT DOCUMENTS

| 7,418,392 | B1 | 8/2008 | Mozer et al. | |
| 7,720,683 | B1 | 5/2010 | Vermeulen et al. | |
| 7,774,204 | B2 | 8/2010 | Mozer et al. | |
| 8,918,209 | B2 * | 12/2014 | Rosenstein et al. | ........... 700/254 |
| 8,922,480 | B1 * | 12/2014 | Freed et al. | ................... 345/156 |
| 2012/0223885 | A1 | 9/2012 | Perez | |

FOREIGN PATENT DOCUMENTS

WO        WO2011088053 A2        7/2011

OTHER PUBLICATIONS

Cochran, Repeated Trials & Expected Values, 2004, pp. 1-5.*
Pinhanez, "The Everywhere Displays Projector: A Device to Create Ubiquitous Graphical Interfaces", IBM Thomas Watson Research Center, Ubicomp 2001, Sep. 30-Oct. 2, 2001, 18 pages.

* cited by examiner

Primary Examiner — Phu K Nguyen
(74) Attorney, Agent, or Firm — Lee & Hayes, PLLC

(57) ABSTRACT

A projection, image, and depth capture system projects content into a scene and captures images of the scene as the user interacts with the content. The system uses depth analysis to determine location and distance of available surfaces in the scene onto which the content can be projected. Due to the complexity of this analysis and the inherent imperfections of the electronic and optical components, depth analysis possesses inherent noise that may adversely affect the accuracy of the projected image onto the surface. The system is configured with noise compensation technology that averages depth information over multiple image frames captured from the scene. The averaged information leads to a more consistent measurement of the distance to the surface, which in turn allows for more accurate focus of the projected content.

23 Claims, 8 Drawing Sheets

APPLICATION SPECIFIC TRACKING OF PROJECTION SURFACES

BACKGROUND

Augmented reality allows interaction among users, real-world objects, and virtual or computer-generated objects and information within an environment. The environment may be, for example, a room equipped with computerized projection and imaging systems that enable presentation of images on various objects within the room and facilitate user interaction with the images and/or objects. The augmented reality may range in sophistication from partial augmentation, such as projecting a single image onto a surface and monitoring user interaction with the image, to full augmentation where an entire room is transformed into another reality for the user's senses. The user can interact with the environment in many ways, including through motion, gestures, voice, and so forth.

As augmented reality systems continue to evolve, there is a continuing need for improved performance of such systems. Designers continue to face tradeoffs between higher precision components, responsiveness, and implementation costs. Accordingly, there is an ongoing desire for new techniques that improve performance without significantly adding costs to the systems.

BRIEF DESCRIPTION OF THE DRAWINGS

The detailed description is described with reference to the accompanying figures. In the figures, the left-most digit(s) of a reference number identifies the figure in which the reference number first appears. The use of the same reference numbers in different figures indicates similar or identical components or features.

DETAILED DESCRIPTION

Figure 1:
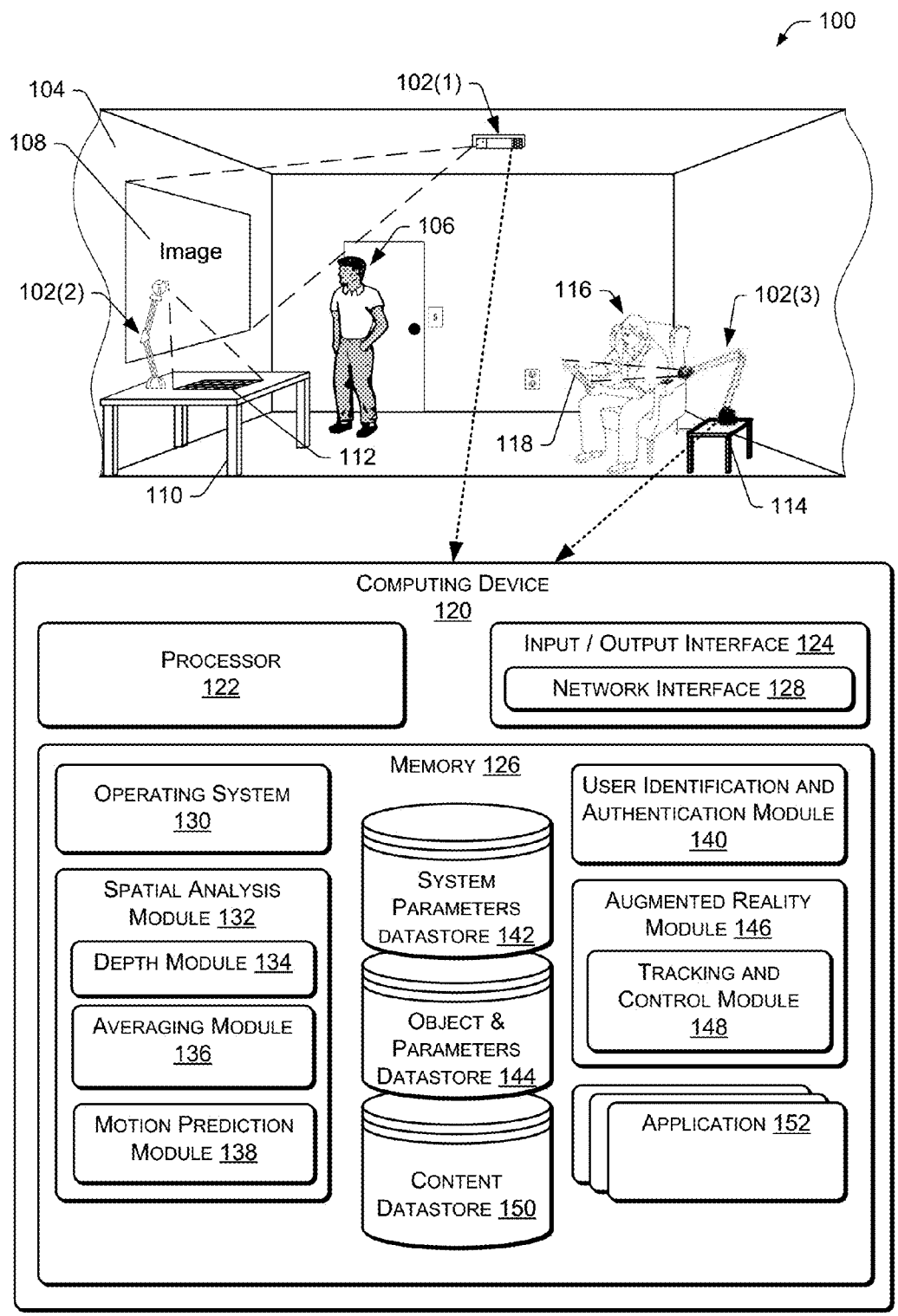
FIG. 1 shows an illustrative scene with an augmented reality environment hosted in an area, such as a room. The augmented reality environment is provided, in part, by three projection, image, and depth capture systems.

Augmented reality environments allow users to interact with physical and virtual objects in a physical space. Augmented reality environments are formed through systems of resources such as cameras, projectors, computing devices with processing and memory capabilities, and so forth. The projectors project images onto the surroundings that define the environment and the cameras monitor and capture user interactions with such images.

An augmented reality environment is commonly hosted or otherwise set within a surrounding area, such as a room, building, or other type of space. In some cases, the augmented reality environment may involve the entire surrounding area. In other cases, an augmented reality environment may involve a localized area of a room, such as a reading area or entertainment area.

Described herein is an architecture to create an augmented reality environment in which a projection, image, and depth capture system projects content onto one or more surfaces in the environment. For instance, the system may project content from an electronic book (or "eBook") or an application such as a browser or other type of navigation user interface onto a wall, or a portable handheld display screen.

The projection, image, and depth capture system includes depth sensing components that allow the system to analyze the spatial characteristics of the environment, including relative location of surfaces and objects. There are various ways to implement depth analysis, including through stereoscopic vision, structured light patterns, and time-of-flight methodologies. For instance, suppose the system is attempting to project an eBook onto a handheld projection screen. The system measures where, within the 3D environment, the user is currently holding the screen and its orientation and rotation. The system then projects a page of content onto the screen.

Due to the complexity of this task and the inherent imperfections of the electronic and optical components, depth analysis possesses inherent noise that may adversely affect the accuracy of the projected image onto the surface. That is, the results of each depth measurement may be slightly inaccurate, causing the focus of the projector to be slightly off when attempting to project content onto a surface. This may cause a less than ideal image on the surface.

The projection, image, and depth capture system is therefore configured with noise compensation techniques that attempt to reduce the adverse impact from the inherent noise. In one implementation, for example, the system captures images of the environment over time and measures or otherwise computes depth information for each image frame. The system then averages the depth information over multiple frames. The averaged information leads to a more accurate measurement of the distance to the surface, which in turn allows for a more accurate focus.

Depending upon the application, there may be more or less tolerance of noise due to the tradeoff between accuracy of the projected content and responsiveness of the system as the content changes. For example, an eBook reader application places a premium on accuracy as the projected text-based content is unlikely to change much over time, making responsiveness less important. In this situation, the noise compensation techniques may average over relatively more frames to more finely tune the projection accuracy. For a gaming application, on the other hand, there may be a higher premium on responsiveness to the changing graphics and less importance placed on accuracy. In this case, the noise compensation techniques may average over comparatively fewer frames, which results in less projection accuracy but allows for more responsiveness to changing content being projected onto the surface.

Additionally, the noise compensation techniques described below enable more precision in gesture or touch recognition. By averaging over multiple frames, the system can make more accurate decisions about when a surface is touched or when a gesture relative to the surface is made. As a result, the user enjoys an improved sense of interaction when working with the surface within the augmented reality environment.

The architecture may be implemented in many ways. One illustrative implementation is described below in which an augmented reality environment is created within a room. The architecture includes one or more projection and camera systems. Multiple implementations of various projection and camera systems are described. For instance, in one implementation, the projection and camera system is implemented to resemble a table lamp. However, the various implementations of the architecture described herein are merely representative.

Illustrative Environment

FIG. 1 shows an illustrative augmented reality environment 100 created within a scene, and hosted within an environmental area, which in this case is a room. Three augmented reality functional nodes (ARFN) 102(1)-(3) are shown within the room. Each ARFN contains at least one projector, one camera, and computing resources that are used to generate the augmented reality environment 100. In other implementations, an individual ARFN may have multiple projectors and/or multiple cameras.

In this illustration, the first ARFN 102(1) is a fixed mount system that may be mounted within the room, such as to the ceiling, although other placements are possible. The ARFN 102(1) includes a projector and an associated camera mounted on a common chassis. The projector projects content onto various surfaces available in the room, such as on the wall (or a screen on the wall), floor, table, and so forth. In this illustration, the ARFN 102(1) is shown projecting an image onto the wall 104. A user 106 may watch and interact with the images being projected onto the wall 104, and the camera of the ceiling-mounted ARFN 102(1) may capture that interaction. One implementation of the first ARFN 102(1) is provided below in more detail with reference to FIGS. 2 and 3.

A second ARFN 102(2) is embodied to resemble a common table lamp, which is shown sitting on a desk 110. The second ARFN 102(2) projects images 112 onto the surface of the desk 110 for the user 106 to consume and/or interact with.

A third ARFN 102(3), also embodied to resemble a table lamp, is shown sitting on a small table 114 next to a chair. A second user 116 is seated in the chair and is holding a portable projection screen 118. The third ARFN 102(3) is equipped with a projector and a camera within the head of the lamp structure. The projector projects content onto a surface of the portable screen 118. The projected content may be any number of things, such as media content (e.g., books, games, news, magazines, movies, etc.) and program content (e.g., email, productivity programs, browser-based applications, etc.).

The portable screen 118 may be essentially any device for use within an augmented reality environment, and may be provided in several form factors. In the implementations described herein, the screen 118 is an entirely passive, handheld, non-electronic device. In such implementations, the passive screen 118 may be embodied with different types of reflective surfaces, including individual features that may receive projected images from an off angle direction and redirect the projected images back along a path that is near normal to the surface of the screen. In other implementations, the screen 118 may be equipped with minimal electronics such as an RFID for identification and registration, and/or an accelerometer for orientation information. In still other implementations, the screen 118 may include increasing complex electronics including processors, memory, and audio input/output. One implementation of the second and third ARFNs 102(2) and 102(3) is provided below in more detail with reference to FIG. 4.

The ARFNs 102(1)-(3) are configured to measure depth within the environment. Through this depth analysis, the ARFNs can ascertain the distance to available surfaces for projection and the location of users and other objects in the room. The ARFNs may use any number of techniques to ascertain distance. For instance, an ARFN equipped with two cameras, or a combination of two or more ARFNs equipped with single cameras, may use stereoscopic methodologies to determine distances within the environment. With the stereoscopic approach, the distance between the two cameras is known, and the two cameras capture images of the scene. The images are compared and depth calculations are derived from the differences between the images and the known distance between the imaging points. In another approach, the ARFNs may emit invisible, structured light onto scene. This invisible light maybe observed and used to determine depth information for surfaces within the environment. In still another approach, the ARFNs may be equipped with time-of-flight (ToF) sensors that emit invisible light (e.g., an IR pulse train) into the environment. The invisible light is scattered by surfaces and objects in the environment, and reflected back to the ARFNs. The ARFNs then measure phase or timing differences in the reflected portions of the invisible light to derive depth information.

In further detail, a ToF camera sensor may comprise a range imaging camera system that resolves distance based on the known speed of light. This sensor measures a time-of-flight of a light signal between the camera and the subject for each point of a captured image. In some instances, ToF sensors represent a class of scannerless LIDAR, in which an entirety of a scene is captured with each emitted laser or light pulse, as opposed to point-by-point with a laser beam such as in scanning LIDAR systems. A ToF sensor may include an illumination component to illuminate the scene, an optical lens to gather the reflected light and image the scene onto an image sensor, the image sensor to determine, for each pixel, how long it took for the emitted light to travel to a surface in the scene and back, and driver electronics to drive the illumination component and the image sensor.

In FIG. 1, the ceiling mounted ARFN 102(1) may use any of the depth techniques to determine the distance to the wall 104. Similarly, the two desktop ARFNs 102(2) and 102(3) may use the structured light and/or ToF techniques to determine depth information for the surface of the table 110 or for the handheld screen 118.

Once the depths are determined, the various ARFNs may run various applications to cause projection of content onto the available surfaces. For instance, the ARFN 102(1) may project images onto the wall to present content such as movies, games, or communication tools (e.g., video conferencing). The second ARFN 102(2) may project images onto the table surface to present content such as a board game, instructions, or educational lessons. The third ARFN 102(3) projects images onto handheld screen 118 to present content such as an electronic book, movie, game, browser, and the like.

With continuing reference to FIG. 1, associated with each ARFN 102(1)-(3) or with a collection of ARFNs, is a computing device 120, which may be located within the augmented reality environment 100 or disposed at another location external to it. Each ARFN 102 may be connected to the computing device 120 via a wired network, a wireless network, or a combination of the two. The computing device 120 has a processor 122, an input/output interface 124, and a memory 126. The processor 122 may include one or more processors configured to execute instructions. The instructions may be stored in memory 126, or in other memory accessible to the processor 122, such as storage in cloud-based resources.

The input/output interface 124 may be configured to couple the computing device 120 to other components, such as projectors, cameras, microphones, other ARFNs, other computing devices, and so forth. It may be further configured with a user interface (UI) to facilitate interaction with the user, such as voice instruction, gesture recognition or motion via the cameras, and so forth. The input/output interface 124 may further include a network interface 128 that facilitates connection to a remote computing system, such as cloud computing resources. The network interface 128 enables access to one or more network types, including wired and wireless networks. More generally, the coupling between the computing device 120 and any components may be via wired technologies (e.g., wires, fiber optic cable, etc.), wireless technologies (e.g., RF, cellular, satellite, Bluetooth, etc.), or other connection technologies.

The memory 126 may include computer-readable storage media ("CRSM"). The CRSM may be any available physical media accessible by a computing device to implement the instructions stored thereon. CRSM may include, but is not limited to, random access memory ("RAM"), read-only memory ("ROM"), electrically erasable programmable read-only memory ("EEPROM"), flash memory or other memory technology, compact disk read-only memory ("CD-ROM"), digital versatile disks ("DVD") or other optical disk storage, magnetic cassettes, magnetic tape, magnetic disk storage or other magnetic storage devices, or any other medium which can be used to store the desired information and which can be accessed by a computing device.

Several modules such as instructions, datastores, and so forth may be stored within the memory 126 and configured to execute on a processor, such as the processor 122. An operating system module 130 is configured to manage hardware and services within and coupled to the computing device 120 for the benefit of other modules.

A spatial analysis module 132 is configured to perform several functions which may include analyzing a scene to generate a 3D model, recognizing objects in the scene, dimensioning the objects, and creating a 3D model of the scene. As discussed previously, characterization may be facilitated using several technologies including structured light, light detection and ranging (LIDAR), optical time-of-flight, ultrasonic ranging, stereoscopic imaging, radar, and so forth either alone or in combination with one another. For convenience, and not by way of limitation, some of the examples in this disclosure refer to stereoscopic imaging, structured light, or optical ToF, although other techniques may be used. The spatial analysis module 132 provides the information used within the augmented reality environment to provide an interface between the physicality of the scene and virtual objects and information.

In some implementations, the spatial analysis module 132 may include a depth module 134 to measure the distance to various surfaces and objects in the environment. In some cases, the depth module may utilize time-of-flight computations for emitted and reflected infrared (IR) signals (or other modulated light output). The time-of-flight value may be derived as a function of a time lapse between emission of the IR light and capture of the IR light from the environment. Alternatively, the time-of-flight value may be derived as a function of the phase difference between the modulated light output and the returned light. In other cases, the depth module 134 may use stereoscopic imaging to map the room or structured light to ascertain depth data. These are merely exemplary and other techniques may be used to measure distances in the environment.

The depth module 134 produces depth data taken at various discrete times or intervals. For instance, a depth camera (e.g., an RBGz camera) may capture images of the environment at various frame rates (e.g., 30 frames per second). Each frame has depth data that defines distances to various surfaces of objects in the environment. The depth data may be expressed in various ways including, for example, as a point cloud where individual points have (x, y, z) coordinates to define a location in space relative to the projection, image, and depth capture system.

The spatial analysis module 132 may further include an averaging module 136 to average the depth information over multiple images of the environment captured over time. For instance, suppose the ARFN routinely captures IR light reflected from the handheld screen 118 and computes optical ToF measurements to determine a distance to the handheld screen 118. This distance information is used to focus the projected content onto the screen's surface. The averaging module 136 may average two or more of the ToF measurements to improve accuracy of the distance information being used to focus the projector.

The number of computations to be averaged may be variable and based upon any number of factors, including the application being executed, the application developer's preferences, default settings, user preferences, environment considerations, or any combination of these. For instance, the averaging module 136 is aware of the application being executed (e.g., an eBook application, a gaming application, a movie application, etc.), and may set the desired sample size to be averaged based on that application. The averaging module 136 may use settings associated with the application, including a default setting and/or one or more pre-defined performance settings designed by the application developers. If the user identity is known, the average module 136 may further consult the user's user profile settings to determine if the user has indicated a preference for higher accuracy in the projected content or better responsiveness.

The number of depth data samples to average may be further based on the scene. If the scene (i.e., the objects/surfaces therein) is relatively static relative to frame rate of capturing images of the environment (e.g., 100 Hz), then the sample size may be increased to improve accuracy. That is, two samples are more accurate than one, and four samples are more accurate than two samples, and so on. Conversely, if the scene is less static relative to the frame rate, there becomes a point where additional samples for computing averages may begin to negatively impact responsiveness. For instance, suppose the user is playing a video game that involves high motion graphics and/or movement of the screen itself. If the scene is dynamic relative to the frame rate, the depth data being computed based on images captured by the ARFN 102(3) will become less accurate fairly quickly and hence fewer samples may be used by the averaging module 136.

In some scenarios, the movement of objects, such as screen 118, may be even more pronounced. Accordingly, the spatial analysis module 132 may further include a motion prediction module 138 to predict movement of an object or display surface within the environment. The motion prediction module 138 may analyze a sequence of frames for movement of the object/surface within the frames. Based on this movement, the motion prediction module 138 may predict where the object/surface will be in the next or future frames. The motion prediction module 138 may compute frame-to-frame deltas, an integral function over multiple frames, or use some other prediction function. In such scenarios, the prediction is applied to the next frame and then that frame is included in the averaging.

The spatial analysis module 132 and various example scenarios involving operation of the depth module 134, the averaging module 136, and the motion prediction module 138 are described below in more detail with reference to FIGS. 5-7.

A user identification and authentication module 140 is stored in memory 126 and executed on the processor(s) 122 to use one or more techniques to verify users within the environment 100. In one implementation, the ARFN 102 may capture an image of the user's face and the spatial analysis module 132 reconstructs 3D representations of the user's face. Rather than 3D representations, other biometric profiles may be computed, such as a face profile that includes key biometric parameters such as distance between eyes, location of nose relative to eyes, etc. In such profiles, less data is used than full reconstructed 3D images. The user identification and authentication module 140 can then match the reconstructed images (or other biometric parameters) against a database of images (or parameters), which may be stored locally or remotely on a storage system or in the cloud, for purposes of authenticating the user. If a match is detected, the user is permitted to interact with the system. In still other implementations, the user identification and authentication module 140 may use audio data captured from the environment to recognize humans in the environment 100. Voice recognition may be used independently of, or together with, visual recognition to enable multiple levels of authentication.

With user identification, the ARFNs 102(1)-(3) can better interact and tailor content for the particular user. For instance, in response to a request from one user, the ARFN may select content or an application suitable for that user. Alternatively, a request from another user may result in the ARFN selecting different content or applications suitable for the other user.

A system parameters datastore 142 is configured to maintain information about the state of the computing device 120, the input/output devices of the ARFN, and so forth. For example, system parameters may include current pan and tilt settings of the cameras and projectors. As used in this disclosure, the datastore includes lists, arrays, databases, and other data structures used to provide storage and retrieval of data. The system parameters datastore 142 may further maintain a user profile containing user preferences. One example preference is an indication of whether the user prefers higher visual accuracy, or better responsiveness.

An object and parameters datastore 144 in the memory 126 is configured to maintain information about the state of objects within the environment and a library of pre-loaded reference objects. The object parameters may include the surface contour of the object, overall reflectivity, color, and so forth. This information may be acquired from the ARFN, other input devices, or via manual input and stored within the object and parameters datastore 144. The library of pre-loaded reference objects may include assumptions about the object, dimensions, and so forth. For example, the datastore 144 may include a reference object of a beverage can and include the assumptions that beverage cans are either held by a user or sit on a surface, and are not present on walls or ceilings.

The spatial analysis module 132 may use the data maintained in the datastore 144 to test dimensional assumptions when determining the dimensions of objects within the scene. For example, objects in the scene which are temporally persistent, such as walls, a particular table, particular users, and so forth may be stored within the object datastore 144. The object datastore 144 may be stored on one or more of the memory of the ARFNs, storage devices accessible on the local network, or cloud storage accessible via a wide area network.

An augmented reality module 146 is configured to generate augmented reality output in concert with the physical environment. The augmented reality module 146 may employ essentially any surface, object, or device within the environment 100 to interact with the users. The augmented reality module 146 may be used to track items within the environment that were previously identified by the spatial analysis module 132. The augmented reality module 142 includes a tracking and control module 148 configured to track one or more items within the scene and accept inputs from or relating to the items. In particular, the tracking and control module 148 is configured to track the portable projection screen 118 as the user 116 holds and moves the screen. The tracking and control module 148 may track orientation, tilt, and position of the screen 118 as the user handles the screen 118.

In some implementations, the augmented reality module 146 cooperates with the special analysis module 132 to get depth data from the depth module 134, or averaged depth data from the averaging module 136, and/or motion information from the motion prediction module 138. In other implementations, these modules 134-138 may reside in the augmented reality module 146 or be replicated therein. In still other implementations, the depth module 134, averaging module 136, and motion prediction module may be separate modules independent of, but accessible by, the special analysis module 132 and/or the augmented reality module 146.

The computing device 120 directs the projectors of the ARFNs to project different images onto the various surfaces. The images may comprise essentially any type of subject matter, including various forms of content and applications. Content is stored in a content datastore 150 or in remote location (not shown) that is accessible by the computing device 120. The content may be any type of electronic renderable content, such as text, audio, images, and video. Example content may include electronic books, music, movies, games, and so on.

One or more applications 152 may be stored on the computer 120 or on an accessible remote location. As the applications are executed by the processor 120, various user interfaces and/or computed results of the applications may be projected by the projector onto the screen. The applications 152 may also have associated settings that specify preferences for accuracy and responsiveness that may be used by the averaging module 136 in determining the number of samples to average. For instance, an eBook application 152 may place a higher premium on accuracy as the reader expects to read words that are clear and finely focused. For a reading experience, the user is expected to hold the screen 118 fairly still, making the scene relatively static as compared the frame rate of captured images of the environment. Accordingly, an eBook application may have preference settings that guide the averaging module 136 to average over many frames to improve the precision and resolution of the letters.

In contrast, a gaming application may place a higher premium on responsiveness as the images are changing quickly. There is less expectation for clarity as some blurring and image movement may be tolerated. For a gaming experience, the scene may be less static as compared the frame rate of captured images of the environment. Accordingly, a gaming application may have preference settings that guide the averaging module 136 to average over fewer frames, thereby attempting to make some improvement to accuracy, but not at the expense of responsiveness.

The ARFNs 102 and computing components of device 120 that have been described thus far may be operated to create an augmented reality environment in which a passive handheld screen may be used to provide multiple user contexts simply by turning different surfaces of the screen toward the ARFN. The users' movements, voice commands, and other interactions are captured by the ARFNs 102 to facilitate user input to the environment.

Representative ARFN Implementations

Figure 2:
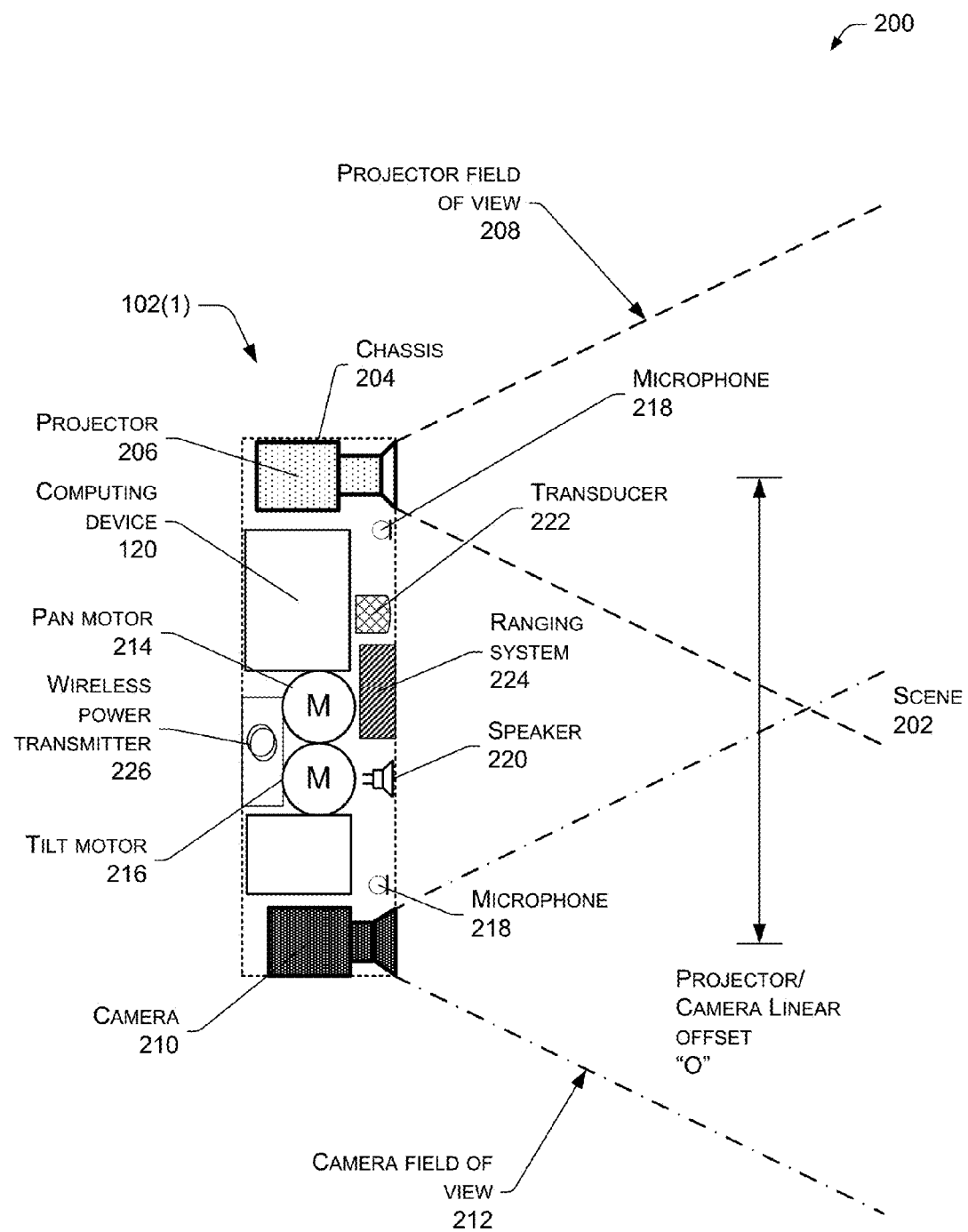
FIG. 2 shows a first implementation of a projection, image, and depth capture system formed as an augmented reality functional node having a chassis to hold a projector and camera in spaced relation to one another. In this implementation, the projector and camera have different optical paths and depth information may be obtained using stereoscopic imaging or use of structured light.
Figure 3:
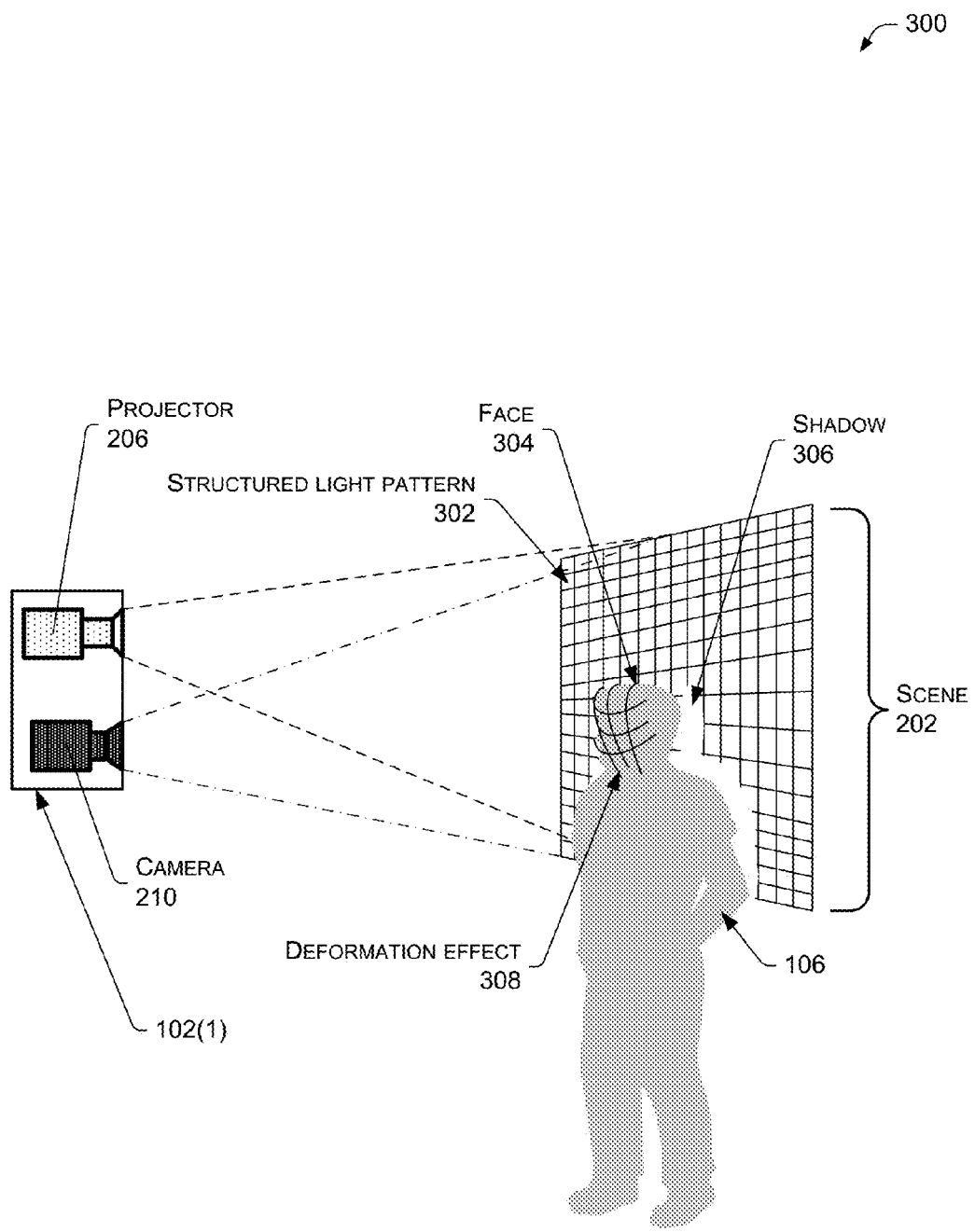
FIG. 3 illustrates one example implementation of creating an augmented reality environment by projecting structured light on a scene in the environment and capturing a corresponding image of the scene.
Figure 4:
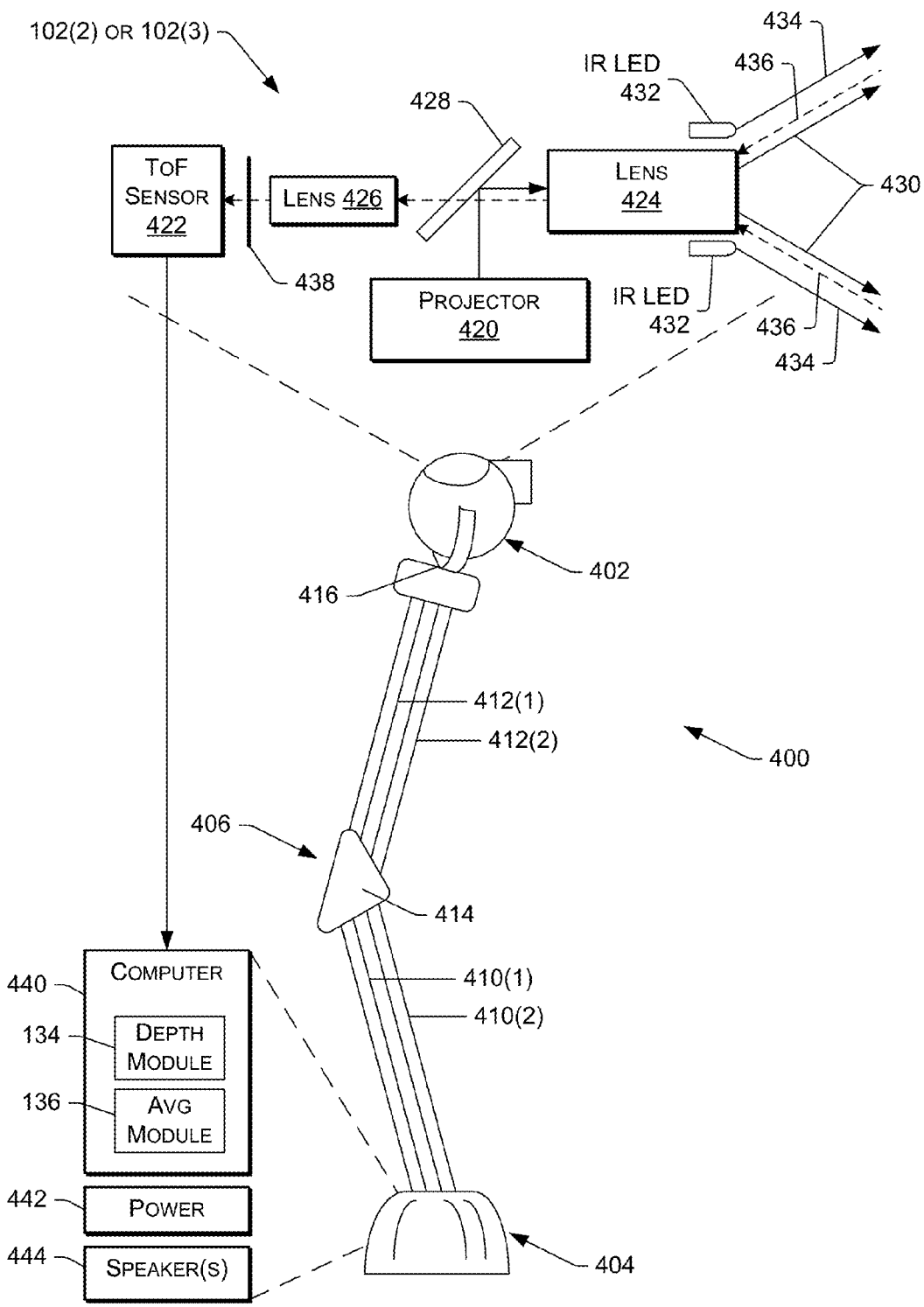
FIG. 4 shows a second implementation of a projection, image, and depth capture system formed to resemble a familiar type of furniture, such as a table lamp. In this implementation, the projector and camera share a common optical path through a lens and depth information is provided through use of a time-of-flight sensor.

Before describing various representative scenarios involving operation of the depth module 134, the averaging module 136, and the motion prediction module 138, the ARFNs 102 (1)-(3) are described in more detail with respect to FIGS. 2-4.

FIG. 2 shows an illustrative schematic 200 of the first augmented reality functional node 102(1) and selected components. The first ARFN 102(1) is configured to scan at least a portion of a scene 202 and the objects within the environment 100. The ARFN 102(1) may also be configured to provide augmented reality output, such as images, sounds, and so forth.

A chassis 204 holds the components of the ARFN 102(1). Within the chassis 204 may be disposed a projector 206 that generates and projects images into the scene 202. These images may be visible light images perceptible to the user, visible light images imperceptible to the user, images with non-visible light, or a combination thereof. This projector 206 may be implemented with any number of technologies capable of generating an image and projecting that image onto a surface within the environment. Suitable technologies include a digital micromirror device (DMD), liquid crystal on silicon display (LCOS), liquid crystal display, 3LCD, and so forth. The projector 206 has a projector field of view 208 which describes a particular solid angle. The projector field of view 208 may vary according to changes in the configuration of the projector. For example, the projector field of view 208 may narrow upon application of an optical zoom to the projector. In some implementations, a plurality of projectors 206 may be used. Further, in some implementations, the projector 206 may be further configured to project patterns, such as non-visible infrared patterns, that can be detected by camera (s) and used for 3D reconstruction and modeling of the environment. The projector 206 may comprise a microlaser projector, a digital light projector (DLP), cathode ray tube (CRT) projector, liquid crystal display (LCD) projector, light emitting diode (LED) projector or the like.

A camera 210 may also be disposed within the chassis 204. The camera 210 is configured to image the scene in visible light wavelengths, non-visible light wavelengths, or both. The camera 210 may be implemented in several ways. In some instances, the camera may be embodied an RGB camera. In other instances, the camera may include ToF sensors. In still other instances, the camera 210 may be an RGBZ camera that includes both ToF and RGB sensors. The camera 210 has a camera field of view 212 which describes a particular solid angle. The camera field of view 212 may vary according to changes in the configuration of the camera 210. For example, an optical zoom of the camera may narrow the camera field of view 212. In some implementations, a plurality of cameras 210 may be used.

The chassis 204 may be mounted with a fixed orientation, or be coupled via an actuator to a fixture such that the chassis 204 may move. Actuators may include piezoelectric actuators, motors, linear actuators, and other devices configured to displace or move the chassis 204 or components therein such as the projector 206 and/or the camera 210. For example, in one implementation, the actuator may comprise a pan motor 214, tilt motor 216, and so forth. The pan motor 214 is configured to rotate the chassis 204 in a yawing motion. The tilt motor 216 is configured to change the pitch of the chassis 204. By panning and/or tilting the chassis 204, different views of the scene may be acquired. The spatial analysis module 114 may use the different views to monitor objects within the environment.

One or more microphones 218 may be disposed within the chassis 204, or elsewhere within the scene. These microphones 218 may be used to acquire input from the user, for echolocation, location determination of a sound, or to otherwise aid in the characterization of and receipt of input from the scene. For example, the user may make a particular noise, such as a tap on a wall or snap of the fingers, which are pre-designated to initiate an augmented reality function. The user may alternatively use voice commands. Such audio inputs may be located within the scene using time-of-arrival differences among the microphones and used to summon an active zone within the augmented reality environment. Further, the microphones 218 may be used to receive voice input from the user for purposes of identifying and authenticating the user. The voice input may be received and passed to the user identification and authentication module 122 in the computing device 104 for analysis and verification.

One or more speakers 220 may also be present to provide for audible output. For example, the speakers 220 may be used to provide output from a text-to-speech module, to playback pre-recorded audio, etc.

A transducer 222 may be present within the ARFN 102(1), or elsewhere within the environment, and configured to detect and/or generate inaudible signals, such as infrasound or ultrasound. The transducer may also employ visible or non-visible light to facilitate communication. These inaudible signals may be used to provide for signaling between accessory devices and the ARFN 102(1).

A ranging system 224 may also be provided in the ARFN 102 to provide distance information from the ARFN 102 to an object or set of objects. The ranging system 224 may comprise radar, light detection and ranging (LIDAR), ultrasonic ranging, stereoscopic ranging, and so forth. In some implementations, the transducer 222, the microphones 218, the speaker 220, or a combination thereof may be configured to use echolocation or echo-ranging to determine distance and spatial characteristics.

A wireless power transmitter 226 may also be present in the ARFN 102, or elsewhere within the augmented reality environment. The wireless power transmitter 226 is configured to transmit electromagnetic fields suitable for recovery by a wireless power receiver and conversion into electrical power for use by active components in other electronics, such as a non-passive screen 118. The wireless power transmitter 226 may also be configured to transmit visible or non-visible light to communicate power. The wireless power transmitter 226 may utilize inductive coupling, resonant coupling, capacitive coupling, and so forth.

In this illustration, the computing device 120 is shown within the chassis 204. However, in other implementations all or a portion of the computing device 120 may be disposed in another location and coupled to the ARFN 102(1). This coupling may occur via wire, fiber optic cable, wirelessly, or a combination thereof. Furthermore, additional resources external to the ARFN 102(1) may be accessed, such as resources in another ARFN accessible via a local area network, cloud resources accessible via a wide area network connection, or a combination thereof.

The ARFN 102(1) is characterized in part by the offset between the projector 206 and the camera 210, as designated by a projector/camera linear offset "O". This offset is the linear distance between the projector 206 and the camera 210. Placement of the projector 206 and the camera 210 at distance "O" from one another aids in the recovery of structured light data from the scene. The known projector/camera linear offset "O" may also be used to calculate distances, dimensioning, and otherwise aid in the characterization of objects within the scene 202. In other implementations, the relative angle and size of the projector field of view 208 and camera field of view 212 may vary. Also, the angle of the projector 206 and the camera 210 relative to the chassis 204 may vary.

Due to this offset "O", the projector 206 and camera 210 employ separate optical paths. That is, the projector 206 employs a set of lenses to project images along a first optical path therein, and the camera 210 employs a different set of lenses to image the scene by capturing the light scattered by the surroundings.

In other implementations, the components of the ARFN 102(1) may be distributed in one or more locations within the environment 100. As mentioned above, microphones 218 and speakers 220 may be distributed throughout the scene. The projector 206 and the camera 210 may also be located in separate chassis 204.

In still other implementations, two or more cameras 210 may be mounted on the same chassis 204, or may be otherwise functionally part of the same ARFN. With two cameras, depth data may be collected using stereoscopic imaging techniques, where two offset images captured by the two cameras are used to gauge depth. This is similar to how humans perceive depth, using images captured by the left and right eyes, which are a known distance apart. The two-dimensional images are then combined in the brain to give the perception of 3D depth.

In addition to stereoscopic imaging, another technique used to discern depth information may employ structured light. FIG. 3 illustrates one example operation 300 of the ARFN 102(1) of creating an augmented reality environment by projecting a structured light pattern on a scene and capturing a corresponding image of the scene. In this illustration, the projector 206 within the ARFN 102(1) projects a structured light pattern 302 onto the scene 202. In some implementations, a sequence of different structure light patterns 302 may be used. This structured light pattern 302 may be in wavelengths which are visible to the user, non-visible to the user, or a combination thereof. The structured light pattern 304 is shown as a grid in this example, but not by way of limitation. In other implementations, other patterns may be used, such as bars, dots, pseudorandom noise, and so forth. Pseudorandom noise (PN) patterns are particularly useful because a particular point within the PN pattern may be specifically identified. A PN function is deterministic in that given a specific set of variables, a particular output is defined. This deterministic behavior allows the specific identification and placement of a point or block of pixels within the PN pattern.

The user 106 is shown within the scene 202 such that the user's face 304 is between the projector 206 and a wall. A shadow 306 from the user's body appears on the wall. Further, a deformation effect 308 is produced on the shape of the user's face 304 as the structured light pattern 302 interacts with the facial features. This deformation effect 308 is detected by the camera 210, which is further configured to sense or detect the structured light. In some implementations, the camera 210 may also sense or detect wavelengths other than those used for structured light pattern 302.

The images captured by the camera 210 may be used for any number of things. For instances, some images of the scene are processed by the spatial analysis module 132 to characterize the scene 202. In some implementations, multiple cameras may be used to acquire the image. In other instances, the images of the user's face 304 (or other body contours, such as hand shape) may be processed by the spatial analysis module 132 to reconstruct 3D images of the user, which are then passed to the user identification and authentication module 140 for purposes of verifying the user.

Certain features of objects within the scene 202 may not be readily determined based upon the geometry of the ARFN 102(1), shape of the objects, distance between the ARFN 102(1) and the objects, and so forth. As a result, the spatial analysis module 132 may be configured to make one or more assumptions about the scene, and test those assumptions to constrain the dimensions of the scene 202 and maintain the model of the scene.

A third technique to ascertain depth information about an environment is through use of time-of-flight (ToF) sensors. To illustrate this technique, another ARFN implementation, as represented by the ARFNs 102(2) and 102(3) in FIG. 1, is described in more detail to explain its use of ToF sensors. In contrast to the design of the first ARFN 102(1), which employs camera and projector linearly offset a pre-known distance and thus involves a comparatively larger form factor, the ARFNs 102(2) and 102(3) remove the offset through a design that allows the projector and camera to share a common optical path. In this design, the form factor may be reduced. In the example shown in FIG. 1, the ARFNs 102(2) and 102(3) are embodied to resemble common table lamps, where the projector and camera reside in a head of the lamp.

FIG. 4 shows one implementation of the ARFN 102(2) or 102(3), implemented to resemble a table lamp, although it may be incorporated into other familiar types of furniture. Further, the optical components described in this implementation may be embodied in non-furniture arrangement, such as a standalone unit placed in the room or mounted to the ceiling or walls (i.e., similar to the ARFN 102(1) described above), or incorporated into fixtures such as a ceiling light fixture. The table lamp 400 has a head 402 attached to a base 404 by a movable arm mechanism 406. As illustrated, the arm mechanism 406 has two base members or rods 410(1) and 410(2) connected to two head members or rods 412(1) and 412(2) via a joint connector 414. Other configurations of the arm mechanism 406 may be used. In the illustrated implementation, the head 402 is connected to the arm mechanism 406 via a universal connector 416 that enables at least two degrees of freedom (e.g., along tilt and pan axes). In other implementations, the head 402 may be mounted to the arm mechanism 406 in a fixed manner, with no movement relative to the arm mechanism 406, or in a manner that enables more or less than two degrees of freedom.

The head 402 holds several components, including a projector 420 and a time of flight (ToF) sensor 422. In this example, the ToF sensor 422 measures IR signal reflections from objects within the scene. The ToF sensor 422 may be implemented as a standalone sensor, or as part of a camera. The head also contains one or more lenses, including a first lens 424 and a second lens 426. The first lens 424 may be implemented in a number of ways, including as a fixed lens, wide angle lens, or as a zoom lens. When implemented as a zoom lens, the lens may have any zoom range, with one example being 17-50 mm. Use of a zoom lens also offers additional advantages in that a zoom lens permits a changeable field of view, which can increase pixel resolution for better gesture recognition. Further, by zooming in, the device can decrease the field of view and enable the ability to discern fingers that were not resolved in non-zoomed (larger field of view) state. The lens 424 may further include a motorized focus, a motorized zoom, and a motorized iris.

The second lens 426 is provided to adjust for the differences between the projection imager and the ToF imager. This allows for the device to set relative coverage of the two imagers (e.g., overscan/underscan). In some implementations, the second lens 426 may not be included.

The projector 420 projects an image that is reflected off an angled beam splitter 428 and out through the lens 424. The beam splitter 428 may be, for example, embodied as a dichroic beam splitter having a coated prism assembly that employs dichroic optical coatings to separate light by wavelengths. The projected image has a field of view represented by the outgoing pair of arrows 430. In this manner, the visible and high intensity light from the projector can be zoomed for image projection on a wide range of surfaces, from near view to far view surfaces.

One or more IR emitters 432, such as IR LEDs, are positioned in the head 402 relative to the lens 424. The IR emitters 432 direct IR light in the direction of the projected image to illuminate the scene onto which the images are being projected. The IR emitters 432 may be arranged such that the illumination field is wider than the projected field, as represented by the outgoing pair of arrows 434.

The IR signals are reflected from objects in the scene and returned to the lens 424, as represented by the incoming pair of arrows 436. The captured IR signals are passed through the lens 424 and through the dichroic beam splitter 428 to the secondary lens 426. The IR signals are then optionally passed through an IR filter 438 (or other filter type) to the ToF sensor 422. In other implementations, the IR signals may be passed directly from the lens 426 to the ToF sensor 422, without going through the IR filter 438. Accordingly, the IR signals are emitted out from the head 402, reflected by the objects, and collected by the head 402 for capture by the ToF sensor 422 as a way to image the scene. This technique is performed in lieu of using structured light, as described above with respect to one implementation of the first ARFN 102(1) shown in FIG. 3.

It is noted that, in other implementations, the projector 420 may be arranged to project an image that is passed through the beam splitter 428 and out through the lens 424, rather than being reflected by the beam splitter 428. In this arrangement, the returning IR signals may be received back through the lens 424 and reflected by the beam splitter 428 to the lens 426 and ToF sensor 422. Said another way, the projector 420 and IR components (i.e., ToF sensor 422, lens 426 and optionally filter 438) may be swapped so that the returning IR signals are reflected by the beam splitter 428 rather than the projected image. Other arrangements may also be possible where at least part of the optical path is shared by the projection and depth capture.

The lamp-based ARFN 102(2) or 102(3) may also be equipped with one or more components in the base 404. In this example, a computer 440 resides in the base 404, along with power components 442 and one or more speakers 444. The computer may include processing and memory to execute instructions.

The depth module 134 may be executed by the computer 440 to measure a time of flight for an IR signal (or other modulated light output). The time-of-flight value may be derived as a function of a time elapsed between emission from an IR LED 432 and capture by the ToF sensor 422. Alternatively, the time-of-flight value may be derived as a function of the phase difference between the modulated light output and the returned light. The depth module may be implemented in software or hardware.

The averaging module 136 may also be executed by the computer 440 to average depth data over multiple frames. The averaging module 136 may average in any number of ways, including pixel by pixel, over sets of pixels, frame-by-frame, or by averaging segmentation data derived from 2D images of the scene.

It is noted that in other implementations, the components shown as residing in the base 404 may reside in the head 402 or arm mechanism 406. For instance, the computer 440 may be located in the head, and the speakers may be 444 may be distributed in multiple locations, including the base, arm mechanism, and/or the head.

Notice that in this implementation of FIG. 4, the projector 420 and the sensor 422 share a common optical path through a common lens 424. As a result, the ARFN may be made more compact to a smaller form factor, as one set of lenses are removed in this design as compared to the offset design for FIG. 2.

Illustrative Scenarios

Figure 5:
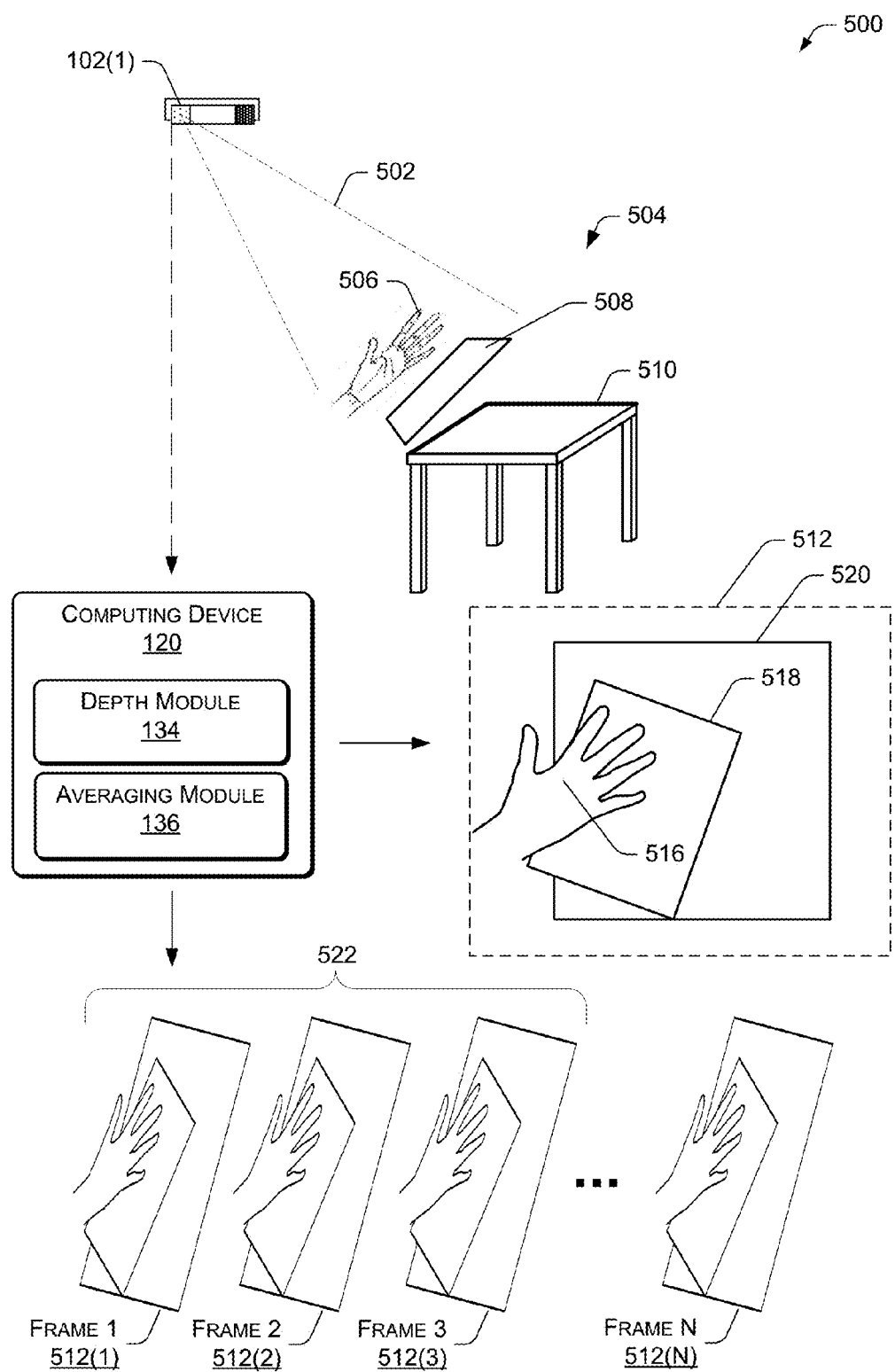
FIG. 5 illustrates how the projection, image, and depth capture system track and analyze projection surfaces in the environment.
Figure 6:
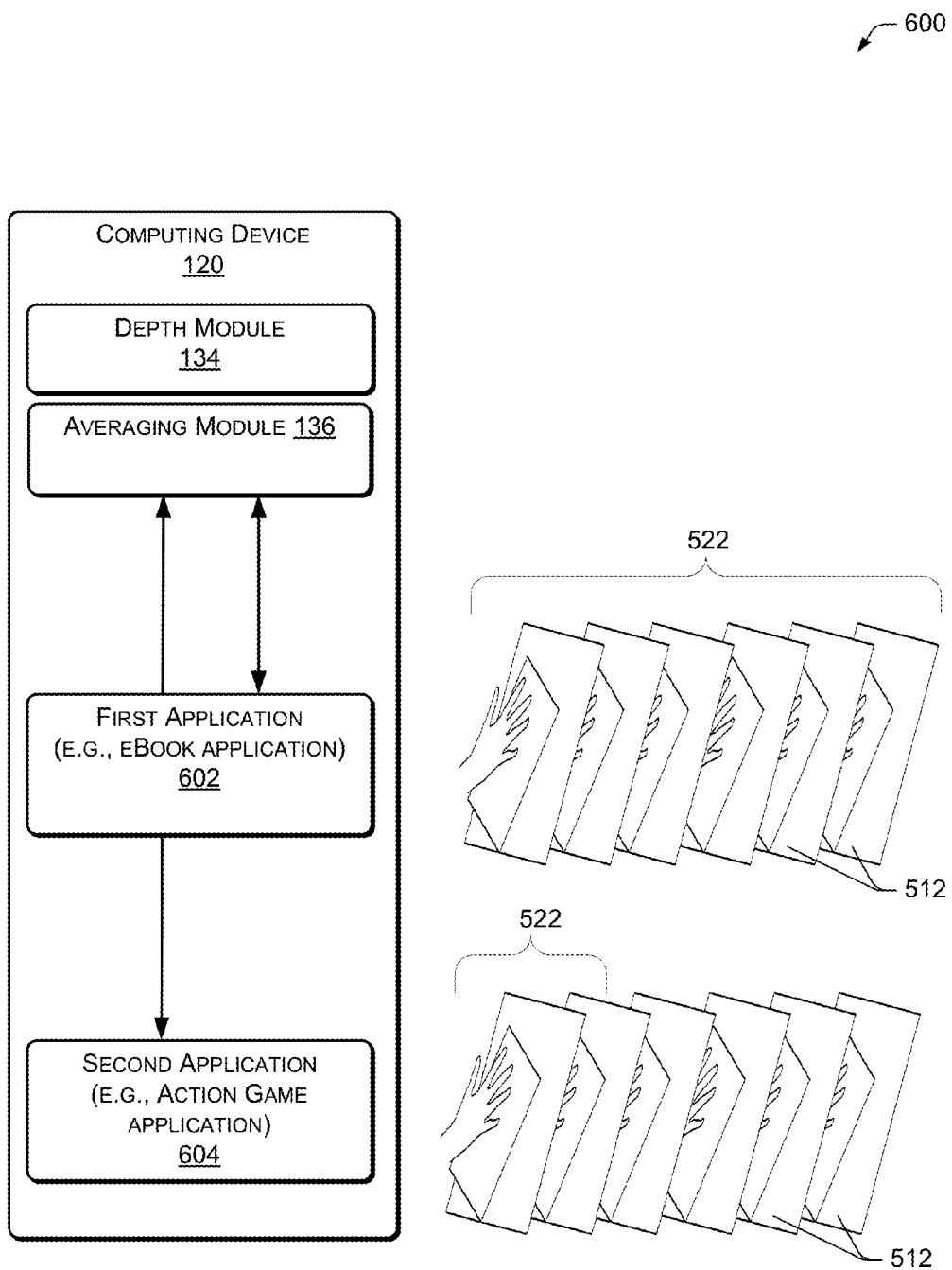
FIG. 6 illustrates how different applications may utilize different averaging parameters in the depth analysis.
Figure 7:
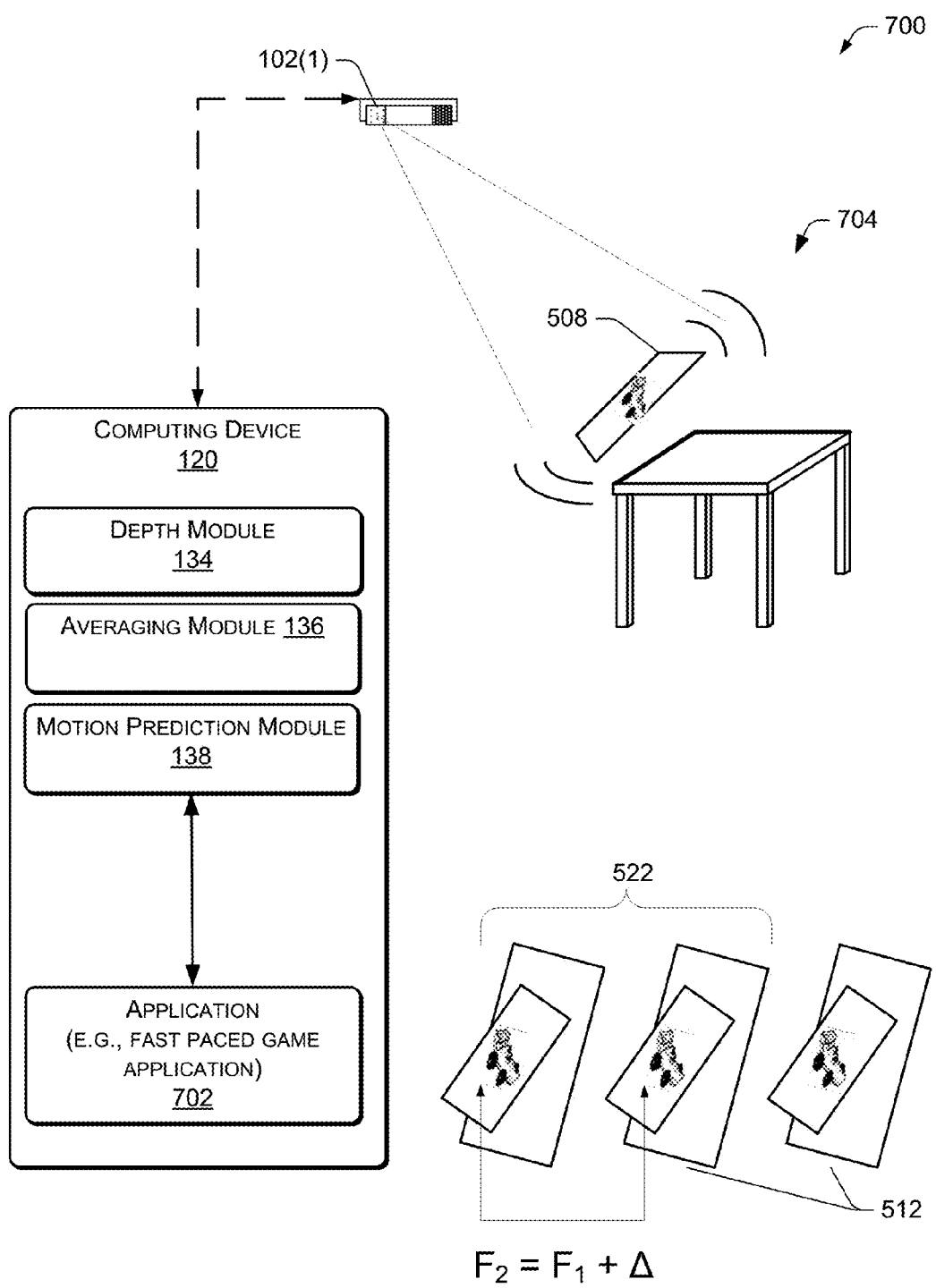
FIG. 7 shows how depth analysis is performed in a scene that involves motion.

FIGS. 5-7 illustrate various representative scenarios in which depth analysis is used to track projection surfaces in the environment. The scenarios are shown as being performed by the ARFN 102(1), although any one of the scenarios may be facilitated by any one of the ARFNs, or other devices that have projector and computing capabilities. Further, these are merely representative of a vast number of scenarios that may be performed according to the techniques described herein.

FIG. 5 illustrates a scenario 500 in which the projection, image, and depth capture system embodied in the ARFN 102(1) uses depth analysis to track and analyze spaces in the environment. The ARFN 102(1) is shown projecting light 502 (visible and/or invisible) into an environment 504. For discussion purposes, the environment 504 includes a human hand 506 (the rest of the body is not shown for clarity), a projection screen 508, and a table 510. In one implementation, the light 502 is IR light that is emitted into the environment 504 and reflected by the hand 506, screen 508, and table 510.

Some of the reflected IR light 502 is captured from the environment by the ARFN 102(1) to produce environment images of the scene. More specifically, the captured IR light 502 is passed to a depth sensor, such as a ToF sensor or RGBZ camera (i.e., a camera equipped with a ToF sensor) of the ARFN 102(1). The data from the depth sensor of the ARFN 102(1) is provided to the computing device 120, where the depth module 134 uses the data to form the images of the scene. The images carry the depth data, and may be analyzed to reconstruct 3D characteristics of the scene 504. The depth data may be structured, for example, as (x, y, z) coordinates in space relative to projector, image, and depth capture system. These coordinates effectively define a 3D point cloud of points defining the various objects in space, including the hand 506, screen 508, and table 510. In one particular implementation, an image from the scene may be segmented. Object segmentation involves performing various types of shape analysis, including 2D and/or 3D techniques, to identify the hand 506, screen 508, and table 510 within the scene 504. In certain implementations, the segmentation uses the depth data from the depth sensor on the ARFN 102(1) to produce an image 512 of the scene 504, which shows a hand contour 516 of the hand 506, a screen contour 518 of the screen 508, and a table surface contour 520 of the table 510. The contours reveal approximate outlines of the objects found in the environment. Objects which are separated in space can be segmented from one another. In this manner, the image 512 includes relative depth information, as the hand contour 516 is closest to the camera of the ARFN 102(1) as detected by it appearing overlaid on the screen contour 518 and surface contour 520. The screen contour 518 is next closest, followed by the table surface contour 520. The contours can be further used to differentiate certain physical characteristics of the objects, such as contour characteristic points of the hand (e.g., finger tips, midpoints along fingers, valleys between fingers, etc.).

The averaging module 136 may then be invoked to average multiple images or frames 512 captured over time. More particularly, the averaging module 136 may be used to average the depth data derived from each of the frame 512. As shown, a sequence of frames 512(1), 512(2), . . . , 512(N) may be captured over time. Each frame carries depth data for various objects in the environment, such as distances to the hand 506, screen 508, and table 510. Depending upon implementation, each frame may be representative of a 3D image, a 2D image, a contour map, a point cloud, and so forth. The number of frames captured per unit time is a parameter that may be set or varied depending upon the usage scenario. One example frame rate might be 100 Hz, where a new frame 512 is captured every 10 milliseconds. Faster or slower frame rates are possible.

The averaging module 136 may average the depth data across any number of frames. For instance, the size of an averaging window 522 might be set to three frames, as shown. In this case, the depth data associated with the first three frames 512(1), 512(2), and 512(3) may be averaged to improve accuracy of the depth information by effectively reducing the impact of inherent noise in the ARFN components from the production of the images 512. Three frames are merely an example, and not a limitation. The number of frames may be any number from two to many. Moreover, the size of the averaging window 522 may be adjustable depending upon the application being executed.

Moreover, in addition to improved projection accuracy, averaging depth data over multiple frames provides for improved touch or gesture recognition. The averaged depth information relative to a surface, as produced by the averaging module 136, may be used by the computing device 120 to more accurately discern when the user touches a projected image on the surface, or makes a gesture relative to the projected image. This improved accuracy facilitates an enhanced user experience when interacting with projected images on objects in the environment.

FIG. 6 illustrates another scenario 600 to show how different applications may utilize different averaging parameters in the depth analysis. Here, a first application 602 may exhibit a preference for higher accuracy in the projected content, even at the expense of any responsiveness degradation. The first application 602 may be representative of an application where the projected images onto a surface involve a high degree of focus and clarity, and where the frame rate is relatively high compared to a fairly still or static projection environment. One example application may be an eBook application or a board game application, where the images are not expected to change much every few seconds.

The first application 602 directs the averaging module 136 to average depth data over a larger number of frames 512. As shown here, the size of averaging window 522 may be six frames. More generally, for such applications with relatively static content, a suitable window size is five or more frames. The averaged data is provided to the ARFN 102(1), which in turn adjusts the projector to more finely focus the projected images onto the surface of the display screen 508.

In contrast, a second application 604 may specify a preference for higher responsiveness of the projected content, even at the expense of accuracy or clarity. The second application 604 may be representative of an application where the projected images onto a surface involve a lot of motion. One example application may be an action game application, such as a shooter game or racing game, where the images change frequently every few second. In this case, the second application 604 directs the averaging module 136 to average a small number of frames 512. As shown here, the size of averaging window 522 may be only two frames. More generally, for such applications with relatively dynamic content, a suitable window size is four or less frames. The averaged data is provided to the ARFN 102(1), which in turn makes slight adjustments to the projector for projection onto the display screen 508.

In some cases, the scene is less static relative to the frame rate. For instance, some gaming applications for fast-paced games may involve moving objects and high motion graphics. In such cases, motion prediction may also be included in the analysis.

FIG. 7 shows still another scenario 700 to illustrate how the depth analysis further takes into account scene motion. In this figure, a gaming application 702 for a fast paced racing game is executing on the computing device 120. As part of this game, the user is encouraged to rotate, twist or otherwise move the hand held screen 508. Accordingly, the computing device 120 may further implement a motion prediction module 138 to predict movement or motion of objects within the scene 704, such as rotation or twisting of the screen 508. Accordingly, as the ARFN 102(1) captures frames 512 of the scene 704, the motion prediction module 138 may first be applied to compensate for movement of the screen 508 within the environment. The motion prediction may be based on a delta frame to frame (e.g., as shown by the frame $F_2$ being a function of the frame $F_1$ plus some delta). Alternatively, an integral of multiple frames may be computed.

After the motion prediction is applied, the averaging module 136 averages the resulting set of frames in the manner as described above.

Illustrative Process

Figure 8:
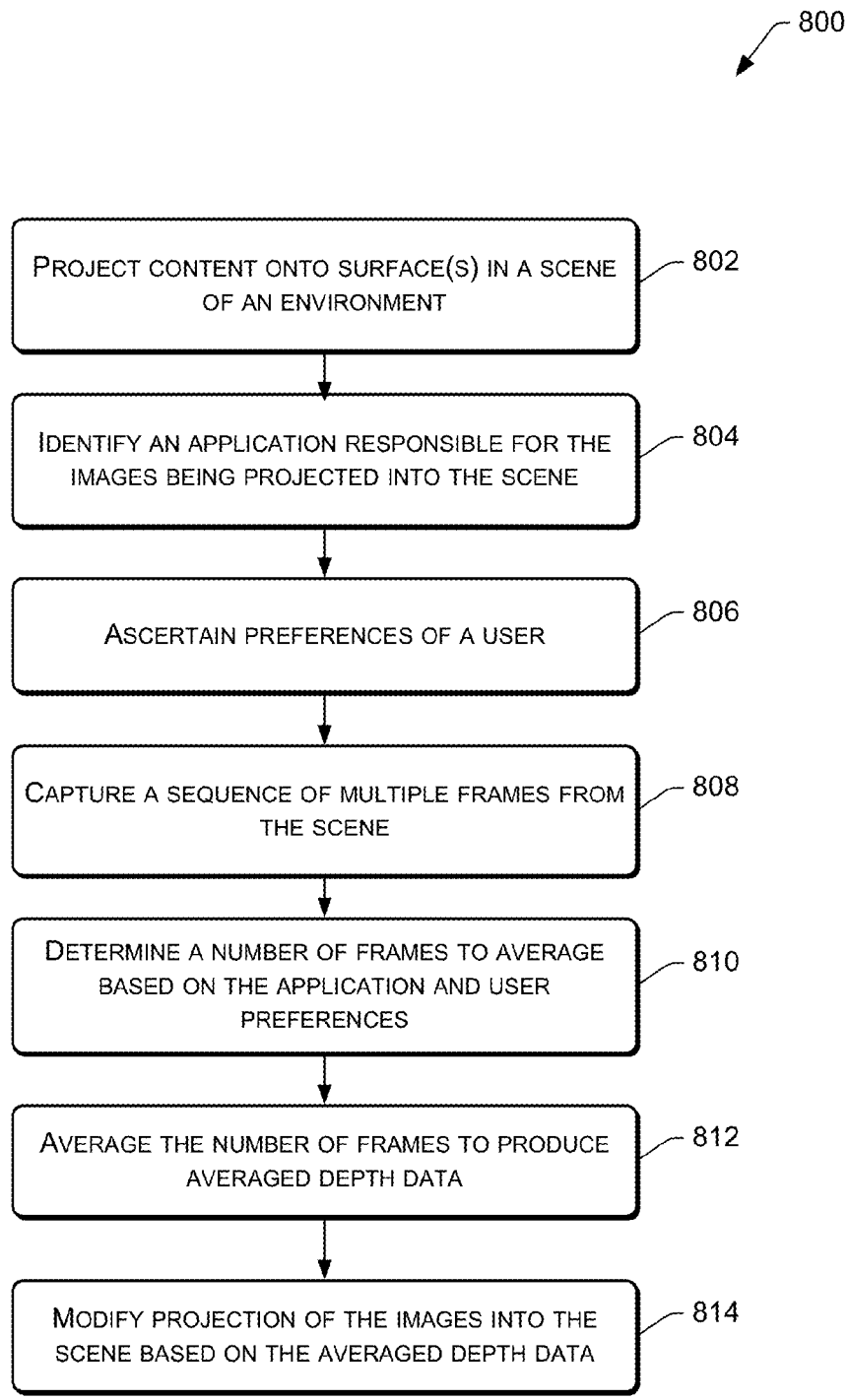
FIG. 8 shows an illustrative process of using a projection, image, and depth capture system in an augmented reality environment to track surfaces in a scene that are available for projection.

FIG. 8 shows an illustrative process 800 of using a projection, image, and depth capture system in an augmented reality environment to more accurately track projection surfaces in a scene. The process described below may be implemented by the architectures described herein, or by other architectures. The process is illustrated as a collection of blocks in a logical flow graph. Some of the blocks represent operations that can be implemented in hardware, software, or a combination thereof. In the context of software, the blocks represent computer-executable instructions stored on one or more computer-readable storage media that, when executed by one or more processors, perform the recited operations. Generally, computer-executable instructions include routines, programs, objects, components, data structures, and the like that perform particular functions or implement particular abstract data types. The order in which the operations are described is not intended to be construed as a limitation, and any number of the described blocks can be combined in any order or in parallel to implement the processes. It is understood that the following processes may be implemented with other architectures as well.

At 802, an application for which images are to be projected onto one or more surfaces in a scene of an augmented reality environment is identified. In one implementation, an ARFN 102 executes an application that defines and/or renders the content and the projector projects the images of the content onto the surface(s). The application may be essentially any application for which visual content is projected in an augmented reality environment. For instance, the application may cause projection of content that remains relatively static in the environment. One example is an eBook reader application which projects eBook content onto a surface and facilitates user navigation of the eBook content (e.g., turning pages) through voice or gesture interaction. Alternatively, the application may cause projection of dynamic content. One example is a gaming application in which the graphical content has a high degree of motion.

At 804, preferences of a user may be ascertained. The user may set preferences regarding the tradeoff between improved accuracy and responsiveness. For instance, the user may be offered a slider control that allows the user to choose along a various range between optimum accuracy and optimum responsiveness.

At 806, content is projected onto the one or more surfaces in a scene of the augmented reality environment. The content may be static in nature (e.g., pictures, text, etc.) or dynamic (e.g., games, etc.).

At 808, a sequence of images is captured from the scene. These images may include structure light distortion, ToF values, and the like that may be used to specify depth information of the surfaces and objects in the scene. In some cases, the image may be processed to segment the various objects and surfaces in the scene. The segmentation process results in 2D contour maps that include the depth information. However, due to the inherent noise in the optical and electronic components, the depth information may not be as accurate as desired by the user.

At 810 and 812, the system uses an averaging technique to improve accuracy by initially determining a number of frames to average based, at least in part, on the application being used and/or the user preferences (810), and then by averaging that number of frames to produce averaged depth data (812). As discussed above with reference to FIGS. 5-7, an averaging module 136 may be used to average two or more frames of captured images in an effort to improve accuracy of the depth information by reducing the effect of the inherent noise. The averaging module 136 may average over more frames in situations where the application and/or user preferences call for improved accuracy, such as where the scene is relatively static compared to the frame rate. Conversely, the averaging module 136 may average over fewer frames in situations where the application and/or user preferences call for responsiveness, such as where the scene is relatively less static compared to the frame rate.

At 814, the averaged depth data is used to more finely focus the projector to modify projection of the content images into the scene. In this manner, the averaged depth data aids in improving the clarity, resolution, or other visual characteristics of the content images.

Conclusion

Although the subject matter has been described in language specific to structural features, it is to be understood that the subject matter defined in the appended claims is not necessarily limited to the specific features described. Rather, the specific features are disclosed as illustrative forms of implementing the claims.

What is claimed is:

1. A system comprising:
   a memory;
   a processor;
   a projector to project content onto a surface in an environment;
   an infrared (IR) emitter to emit IR light onto the surface in the environment;
   a depth sensor to receive at least a portion of the IR light reflected from the surface and to produce depth data at discrete times for use in determining a distance to the surface;
   an analysis module stored in the memory and executed on the processor to receive the depth data produced the depth sensor and to average the depth data produced over multiple discrete times to produce averaged depth data, wherein the averaged depth data is used at least in part to focus the projector for projection of the content onto the surface;
   a first application stored in the memory and executed by the processor to provide first content for projection by the projector, wherein the analysis module is configured to average the depth data over a first number of the multiple discrete times when the first application is being executed to provide content for projection; and
   a second application stored in the memory and executed by the processor to provide second content for projection by the projector, the second content being different from the first content, wherein the analysis module is configured to average the depth data over a second, different number of the multiple discrete times when the second application is being executed to provide content for projection.

2. The system of claim 1, wherein the depth sensor comprises a time-of-flight sensor.

3. The system of claim 1, further comprising user preferences stored in the memory, wherein the analysis module is configured to average the depth data over a number of the multiple discrete times, the number being selected based at least in part on the user preferences.

4. A system comprising:
   one or more components to produce depth data indicative of a distance from the one or more components to at least one surface in an environment onto which content may be projected; and
   an analysis module to:
      determine one of (i) an application associated with content being projected by the system or (ii) a type of the content being projected by the system;
      determine a time over which to average the depth data based at least in part on the application or the type of the content;
      average the depth data over the time to produce averaged depth information; and
      determine the distance to the surface based at least in part on the averaged depth information.

5. The system of claim 4, wherein the one or more components comprise an infrared (IR) emitter to emit IR light onto the surface and a depth sensor to receive at least a portion of the IR light reflected from the surface.

6. The system of claim 4, wherein the one or more components comprise a projector to project structured light onto the environment and a camera to capture images of the environment when the structured light is projected onto the environment.

7. The system of claim 4, wherein the one or more components comprise a time-of-flight sensor.

8. The system of claim 4, wherein the one or more components comprise multiple imaging devices to produce stereoscopic images of the environment.

9. The system of claim 4, further comprising a computing device to determine, based at least in part on the averaged depth information, when a user touches the surface or performs a gesture relative to the surface.

10. One or more non-transitory computer-readable media storing computer-executable instructions that, when executed by one or more processors, cause the one or more processors to perform acts comprising:
- identifying an application that is used to provide content for projection onto a surface in an environment;
- capturing a sequence of images over time, the images including at least part of the surface;
- producing, using each image of the sequence, depth data for use in determining a distance to the surface;
- selecting, based at least in part on the application, a number of the images over which to average the depth data to produce averaged depth information; and
- averaging the depth data associated with each image of the sequence to produce averaged depth information, wherein the number of the images in the sequence over which the depth data is averaged is the number of images.

11. The one or more non-transitory computer-readable media of claim 10, wherein the number of images over which to average is greater when the content provided by the application is static content as compared to when the content provided by the application is dynamic content.

12. The one or more non-transitory computer-readable media of claim 11, wherein the number of images over which to average is more than five when the content provided by the application is static content.

13. The one or more non-transitory computer-readable media of claim 11, wherein the number of images over which to average is less than four when the content provided by the application is dynamic content.

14. The one or more non-transitory computer-readable media of claim 10, the acts further comprising adjusting projection of the content onto the surface in the environment based at least in part on the averaged depth information.

15. The one or more non-transitory computer-readable media of claim 14, the acts further comprising predicting movement of the surface within the environment, wherein the predicted movement is used in part to adjust projection of the content.

16. The one or more non-transitory computer-readable media of claim 10, the acts further comprising identifying, based at least in part on the averaged depth information, at least one of a user touching the surface or the user performing a gesture relative to the surface.

17. A method comprising:
- projecting content onto a surface in an environment;
- generating depth data indicative of a distance to the surface;
- determining one of (i) an application associated with the projected content or (ii) a type of the projected content being projected by the system;
- determining a time over which to average the depth data based at least in part on the application or the type of the projected content;
- averaging the depth data over the time to produce averaged depth information;
- determining the distance to the surface based at least in part on averaged depth information; and
- modifying projection of the content based at least in part on the averaged depth information.

18. The method of claim 17, wherein the generating depth data comprises using stereoscopic imaging to produce the depth data.

19. The method of claim 17, wherein the generating depth data comprises using structured light projected into the environment to produce the depth data.

20. The method of claim 17, wherein the generating depth data comprises using time-of-flight sensors to produce the depth data.

21. The method of claim 17, wherein the generating depth data and averaging the depth data comprises:
- capturing images of the environment;
- generating the depth data using the images;
- averaging the depth data generated using the images to produce the averaged depth information.

22. A method comprising:
- projecting content onto a surface in an environment;
- generating depth data indicative of a distance to the surface;
- determining one of (i) an application associated with the projected content or (ii) a type of the projected content being projected by the system;
- determining a time over which to average the depth data based at least in part on the application or the type of the projected content;
- averaging the depth data over the time to produce averaged depth information;
- determining the distance to the surface based at least in part on averaged depth information; and
- identifying, based at least in part on the averaged depth information, when a user touches the surface or performs a gesture relative to the surface.

23. The method of claim 22, wherein the generating depth data comprises using at least one of (1) stereoscopic imaging to produce the depth data, (2) structured light projected into the environment to produce the depth data, or (3) time-of-flight sensors to produce the depth data.

* * * * *